(12) United States Patent  (10) Patent No.: US 7,340,026 B2
Köhler et al.  (45) Date of Patent: Mar. 4, 2008

(54) RECONSTRUCTION OF THE CURRENT FLOW IN A VESSEL SYSTEM

(75) Inventors: Thomas Köhler, Norderstedt (DE); Michael Grass, Buchholz in der Nordheide (DE)

(73) Assignee: Koninklijke Philips Electronics, N.V., Eindhoven (NL)

( * ) Notice: Subject to any disclaimer, the term of this patent is extended or adjusted under 35 U.S.C. 154(b) by 45 days.

(21) Appl. No.: 10/563,844

(22) PCT Filed: Jun. 29, 2004

(86) PCT No.: PCT/IB2004/051043

§ 371 (c)(1),
(2), (4) Date: Jan. 5, 2006

(87) PCT Pub. No.: WO2005/004038

PCT Pub. Date: Jan. 13, 2005

(65) Prior Publication Data

US 2006/0188138 A1 Aug. 24, 2006

(30) Foreign Application Priority Data

Jul. 8, 2003 (EP) .................................. 03102049

(51) Int. Cl.
*A61B 6/00* (2006.01)
(52) U.S. Cl. .............................. 378/4; 378/62; 378/901; 382/130; 600/431
(58) Field of Classification Search .................... 378/4, 378/62, 901; 600/425, 431; 382/130
See application file for complete search history.

(56) References Cited

U.S. PATENT DOCUMENTS

| 5,671,265 | A | 9/1997 | Andress .................... 378/98.11 |
| 2002/0041654 | A1 | 4/2002 | Hayashi |
| 2003/0040669 | A1 | 2/2003 | Graas et al. ................. 600/407 |
| 2003/0048935 | A1 | 3/2003 | Keren ......................... 382/130 |
| 2003/0114750 | A1 | 6/2003 | Brock-Fisher et al. ....... 600/431 |
| 2003/0123606 | A1 | 7/2003 | Mollus et al. ................ 378/42 |

FOREIGN PATENT DOCUMENTS

DE 19826987 A 12/1999

OTHER PUBLICATIONS

M.Grass, et al: Three-Dimensional Restruction of High Contrast Objects Using C-Arm Image Intensifier Projection Data, vol. 23, 1999, pp. 311-321.
H.Schmitt, et al: An-X-Ray-Based Method for the Determination of the Contrast Agent Propagation in 3-D Vessel Structures, IEEE, vol. 21, No. 3, Mar. 2002, pp. 251-262.

*Primary Examiner*—Courtney Thomas

(57) ABSTRACT

The invention relates to a method of reconstructing the current flow, or the bolus arrival times, in a vessel system. For the sections (i) of the vessel tree, bolus arrival times ($m_i$) are measured, for example in connection with an injection of contrast medium. Based on this measured data, linear programming is then used to calculate model bolus arrival times ($t_i$), which, on the one hand, through minimization of the function $E=\Sigma|m_i-t_i|$, are as close as possible to the measured data, and, on the other, by adherence to the boundary condition $\Delta_i = t_i - t_{p(i)} \geq 0$, ensure the monotony of the propagation, wherein $p(i)$ is the index of the vessel section in front of vessel section (i). Preferably, as smooth as possible a progression is compelled by means of an additional minimization of $E_m = \Sigma|t_i''|$.

10 Claims, 2 Drawing Sheets

$$\vec{a} = \begin{pmatrix} \vec{t} \\ \vec{\epsilon}^+ \\ \vec{\epsilon}^- \\ \vec{\Delta} \\ \vec{\delta}^+ \\ \vec{\delta}^- \end{pmatrix} \quad (26)$$

$$\vec{c} = \begin{pmatrix} \vec{0}_N \\ \vec{1}_N \\ \vec{1}_N \\ \vec{0}_{N-1} \\ \lambda \vec{1}_I \\ \lambda \vec{1}_I \end{pmatrix} \quad (28)$$

$$\vec{b} = \begin{pmatrix} \vec{m} \\ \vec{0}_{N-1} \\ \vec{0}_I \end{pmatrix} \quad (27)$$

$$S = \begin{pmatrix} 1_{N \times N} & 1_{N \times N} & -1_{N \times N} & 0_{N \times N-1} & 0_{N \times I} & 0_{N \times I} \\ P & 0_{N-1 \times N} & 0_{N-1 \times N} & -1_{N-1 \times N-1} & 0_{N \times I} & 0_{N \times I} \\ C & 0_{I \times N} & 0_{I \times N} & 0_{I \times N-1} & 1_{I \times I} & -1_{I \times I} \end{pmatrix} \quad (29)$$

$$C_{ij} = \begin{cases} 2 & \text{if } i = j \\ -1 & \text{if } p(i) = j \\ -1/|\{k|p(k) = i\}| & \text{if } p(j) = i \\ 0 & \text{else} \end{cases} \quad (30)$$

$$\vec{a} = \begin{pmatrix} \vec{t} \\ \vec{\epsilon}^+ \\ \vec{\epsilon}^- \\ \vec{\Delta} \\ \vec{\delta}^+ \\ \vec{\delta}^- \end{pmatrix} \quad (32)$$

$$\vec{c} = \begin{pmatrix} \vec{0}_N \\ \vec{0}_N \\ \vec{0}_N \\ \vec{0}_{N-1} \\ \vec{1}_I \\ \vec{1}_I \end{pmatrix} \quad (34)$$

$$\vec{b} = \begin{pmatrix} \vec{m} \\ \vec{0}_{N-1} \\ \vec{0}_I \\ sE^{(0)} \end{pmatrix} \quad (33)$$

$$S = \begin{pmatrix} 1_{N \times N} & 1_{N \times N} & -1_{N \times N} & 0_{N \times N-1} & 0_{N \times I} & 0_{N \times I} \\ P & 0_{N-1 \times N} & 0_{N-1 \times N} & -1_{N-1 \times N-1} & 0_{N \times I} & 0_{N \times I} \\ C & 0_{I \times N} & 0_{I \times N} & 0_{I \times N-1} & 1_{I \times I} & -1_{N-M \times I} \\ 0_{1 \times N} & 1_{1 \times N} & -1_{1 \times N} & 0_{1 \times N-1} & 0_{1 \times I} & 0_{1 \times I} \end{pmatrix} \quad (35)$$

$$t_i^{(1)} = \begin{cases} t_i^{(0)} & \text{if } i < N \\ t_N^{(0)} - (s-1)E^{(0)} & \text{if } i = N \text{ and } t_N \leq m_N \\ t_N^{(0)} - 2(t_N^{(0)} - m_N) - (s-1)E^{(0)} & \text{if } i = N \text{ and } t_N > m_N \end{cases} \quad (36)$$

Fig. 3

RECONSTRUCTION OF THE CURRENT FLOW IN A VESSEL SYSTEM

The invention relates to a data processing device and a method of reconstructing the current flow in a vessel system, and to an assembly that comprises a data processing device of this kind.

Known from U.S. 2002/0041654 A1 is an X-ray device with which the propagation of an injection of contrast medium in the vessel system of a patient can be observed. The user hereby has to move the X-ray apparatus during the propagation of the contrast medium in order to maintain the propagation front in the image. In order to be able to execute this movement process without a radiation loading on the patient, a simulated contrast-medium propagation is shown on a monitor using stored pictures. Modeling of the actual current flow is not provided with this system.

Against this background, it was an object of the present invention to provide means for reconstructing the current flow in a vessel system, which means enable modeling of the actual circumstances as precisely as possible.

This and other objects are achieved by, e.g., (1) a data processing device with memory including measurement data describing an observed progressive propagation of a medium in a vessel system, the data processing device preferably being equipped so as to be able to reconstruct, from measurement data, one or more model propagations of a medium in a vessel system such that in the vessel system: (i) a difference between an observed propagation and a model propagation is minimal, and (ii) a model propagation is monotonously progressive, (2) an assembly with an image-generating device for generating images of a vessel system, from which measurement data describing the progressive propagation of a medium may be obtained, and a data processing device, such as just herein, for reconstructing current flow in a vessel system, and (3) a method including at least the steps of: (a) obtaining measurement data ($m_i$) describing an observed progressive propagation of a medium in a vessel system, (b) reconstructing a model propagation ($t_i$) of a medium in a vessel system such that: (i) a difference between an observed propagation and a model propagation is minimal, and (ii) a model propagation is monotonously progressive. Advantageous, exemplary embodiments are herein described.

The data processing device in accordance with the invention serves for the reconstruction of the current flow in a vessel system. The vessel system may be, in particular, a section of the blood vessels that is of interest, e.g. the system of coronary vessels, without, however, the invention being restricted to this application example. The data processing device comprises a memory containing measurement data describing an observed progressive propagation of a (first) medium in the said vessel system. This medium may, in principle, be any object that executes a progressive movement through the vessel system. The medium may be, in particular, a fluid flowing within the vessel system, such as an injection of a contrast medium. The propagation of the medium may be described by means of the measured progression over time of the position of the medium, for example of the position of a contrast-medium front or a contrast-medium concentration maximum. This data processing device is equipped to reconstruct, from the said measurement data, a modeled propagation, or "model propagation", of a second medium within the vessel system. The second medium may be identical with the first, or may differ from it (e.g. contrast medium vs. blood). In reconstructing the "model propagation", the following two conditions are to be fulfilled for the vessel system under observation:

firstly, the difference between the observed propagation and the model propagation is to be minimal. In other words, the model propagation sought should follow the measurement data as closely as possible.

secondly, the model propagation is to be monotonously progressive in relation to the vessel system. This means that, in accordance with the model propagation, a medium can move through the vessel system only "forwards" in one direction.

With the data processing device described, it is possible to reconstruct a model consistently and in a stable manner from measurement data concerning the propagation of a (first) medium in a vessel system. This is accomplished by matching a model function to the measurement data globally, i.e. taking into account the entire vessel system under observation, wherein the necessary boundary condition of monotonous propagation is simultaneously observed. If, for example, the propagation of a contrast-medium injection within the vessel system of a patient is measured with X-ray images, strongly divergent data arises in practice as a result of numerous interference effects. It may be, in particular, hereby that no monotonous, i.e. constantly progressing, propagation of the injection is described by the data, but, rather, that jumps and/or backflow are occurring. By contrast, monotony is strictly observed when calculating the model propagation for the entire vessel system, as a result of which, on the one hand, a compulsory boundary condition is fulfilled and, on the other, a significant stabilization of the current reconstruction is achieved.

In accordance with a first further embodiment of the data processing device, the reconstruction is executed in such a way that the model propagation additionally has as smooth as possible a progression. If the model propagation is described generally as a function $f(\tau)$ of a variable A, the "smooth progression" may be defined, in particular, to the effect that the sum of the second derivative, $|f''|$, is to be minimal on average. If $f(\tau)$ is, for example, the position of a propagation front at time $\tau$, then the smoothness clearly corresponds to a propagation that is as low-acceleration as possible.

In accordance with a further preferred embodiment of the data processing device, the memory contains, as measurement data, bolus arrival times $m_i$. The vessel system is hereby logically divided into individual sections, which are identified by the indices $i=1, \ldots N$, and the bolus arrival time $m_i$ is defined as the time determined in a measurement which a (first) medium requires, starting from a predetermined starting point, to reach the vessel section with index i. On the one hand, the discretization of the problem on which this embodiment is based is well suited to handling in a digital data processing device, on the other, it also accords with the fact that the observed propagation of a medium is generally sampled by means of measurements at discrete moments.

As a further development of the embodiment described above, the data processing device is further equipped to calculate model bolus arrival times $t_i$ for the vessel sections i in such a way that the following two conditions are fulfilled:

$$\Delta_i = t_i - t_{p(i)} \geq 0 \ \forall \ i = 1, \ldots N-1 \qquad (1)$$

and $$E = \sum_{i=1}^{N} |m_i - t_i| \text{ is minimal} \qquad (2a)$$

Equation (1) expresses the requirement for a monotonously progressing propagation, whilst (2a) requires, globally for the vessel system, that the model bolus arrival times $t_i$ should follow, as closely as possible, the observed bolus arrival times $m_i$. The values p(i) each hereby reflect the index of the vessel section which, viewed in the direction of flow, is located in front of the vessel section with index i.

In addition, the above-described data processing device may also be supplemented to the effect that the following requirement is additionally taken into account:

$$E_m = \sum_{i \in I} |t_i''| \text{ is minimal} \quad (2b)$$

wherein the quantity 1 contains the indices of all "internal" vessel sections with a predecessor and a successor, and $t_i''$ is the discrete approximation of the second derivative in vessel section i. The condition (2b) expresses the requirement for as smooth as possible a progression of the model bolus arrival times $t_i$. With the combination of the requirements (2a) and (2b), a weighting factor will generally have to be assigned, the defining of which enables the relative significance of the two criteria to be weighted as desired.

In the case of a further development of the embodiment described above, the data processing device is equipped to calculate the model bolus arrival times $t_i$ using the algorithm of linear programming. In the formulation according to equations (1), (2a) and, where applicable, (2b), the model bolus arrival time sought may be regarded as the solution to a linear optimization problem, so recourse may be had to algorithms of linear programming developed for the purpose, such as the Simplex method.

In particular, a three-dimensional model of the vessel system in which the current flow is to be reconstructed may be stored in the memory. Three-dimensional vessel models are increasingly encountered within the context of medical applications, and are of great value in the interpretation of data by the administering doctor.

In accordance with another further embodiment of the data processing device, it may be equipped to take account of physiological boundary conditions in the reconstruction of the model propagation. For example, during an injection of contrast medium, account may be taken of the preservation of the injected contrast-medium mass on its propagation in the vessel system if the measurement data used to describe the propagation, or the model propagation sought, makes provision for the mass value to be taken into account. By taking account of physiological boundary conditions that necessarily have to be fulfilled, the calculated model propagation may be further stabilized against interference effects.

The data processing device is further preferably coupled with a display device, such as a monitor, in order that the calculated model propagation may be graphically represented there. In this manner, the results of the calculation may be made available visually to, for example, an administering doctor in a catheter investigation.

The invention further relates to an assembly for observation of the current flow in a vessel system, wherein the assembly comprises an image-generating device for generating images of the vessel system, and wherein measurement data describing the progressive propagation of a medium in the vessel system may be obtained from the said images. The assembly further comprises a data processing device of the type explained above for reconstructing the current flow in the vessel system. This means that the data processing device comprises a memory with measurement data, which describes the observed progressive propagation of a (first) medium, and which has been obtained by the image-generating device. The data processing device is further equipped to calculate, globally for the vessel system under observation, a model propagation of the (second) medium, which minimizes the difference between the observed and the modeled propagation, and simultaneously describes a monotonous propagation.

The image-generating device may be, in particular, an X-ray apparatus, preferably a rotating X-ray device for generating three-dimensional X-ray images of a body. Equipment of this kind is generally available as a matter of course in catheter laboratories and can therefore be used without problems for a determination of the propagation of an injection of contrast medium and thereby of the flow characteristics in the vessel system of a patient.

The invention further relates to a method of reconstructing the current flow in a vessel system, comprising the following steps:

a) Obtaining measurement data describing an observed progressive propagation of a medium in the vessel system.

b) Reconstructing a model propagation of a medium in the vessel system in such a way that:

the difference between the observed propagation and the model propagation is minimal, and the model propagation is monotonously progressive.

The method implements, in a general form, the steps that can be executed with the above-described data processing device or assembly. To explain the method and the variants that are possible, you are therefore referred to the above description.

The invention will be further described with reference to examples of embodiments shown in the drawings, to which, however, the invention is not restricted.

FIG. 3 shows some of the equations required for the linear programming.

Figure 1:
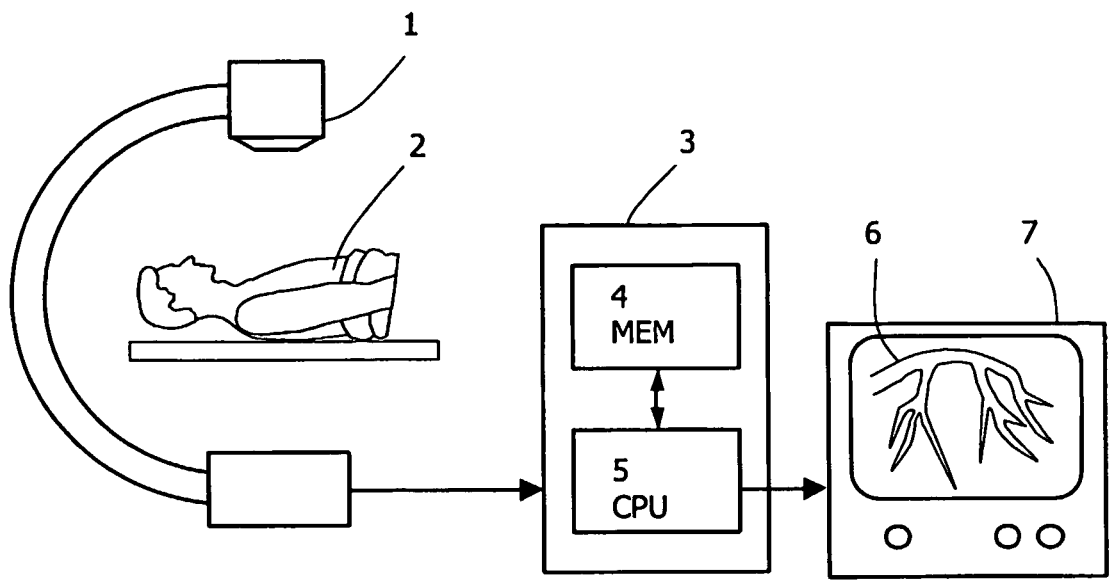
FIG. 1 shows, schematically, the components of an X-ray assembly in accordance with the invention for reconstructing the current flow in a vessel system.

FIG. 1 shows, as a typical example of the use of the present invention, a medical X-ray device. This comprises an X-ray apparatus 1, which is affixed to a C-arm and can rotate about a patient 2 in order to produce X-ray images. The recorded data is passed on to a data processing device 3 for further processing.

The X-ray apparatus 1 may, in particular, be equipped to generate three-dimensional reconstructions of a body volume in order that, for example, the spatial structure of a vessel system may be investigated. Further, the attempt has been made to reconstruct sequences over time, such as, in particular, the flow or propagation of a fluid in the vessel system (see H. Schmitt, M. Grass, V. Rasche, O. Schramm, S. Haehnel, K. Sator: "An X-ray-based method for the determination of the contrast agent propagation in 3-D vessel structures", IEEE Trans. Med. Imag., 21(3):251-262, 2002). These kinds of "4D images" encounter considerable technical problems, for example the necessity for high image rates to record the current flow, the stability of the volume segmentation (i.e. assignment of voxels to objects) and movement correction. In addition, there is the fundamental problem of a good flow reconstruction for an entire vessel system. In this regard, according to the prior art, bolus arrival times (BAT) are determined from the X-ray images for the vessel tree, and assigned to the vessel tree. However, the data thereby obtained shows a severe scatter, which is due inter alia to noise in the X-ray images used, inaccuracies during segmentation, incomplete movement correction or imprecise determination of the bolus arrival times.

Against this background, a method for a stable, reliable reconstruction of the flow characteristics in a vessel system will be explained below with reference to FIGS. 1 to 3. The method begins with a three-dimensional reconstruction of the vessel tree 6, based on rotatory 3D X-ray images. Details of this reconstruction may be found in the relevant literature (e.g. M. Grass, R. Koppe, E. Klotz, R. Proksa, M. H. Kuhn, H. Aerts, J. Op de Beek, R. Kemkers: "3D reconstruction of high contrast objects using C-arm image intensifier projection data", Comput. Med. Imaging Graph., 23:311-321, 1999; M. Grass, R. Koppe, E, Klotz, J. Op de Beek, R. Kemkers: "3D reconstruction and imaging based on C-arm systems", Med. Biol. Eng. Comp., 37(2):1520-1521, 1999). Following segmentation of the vessels, the structure of the vessel tree 6 is known.

Figure 2:
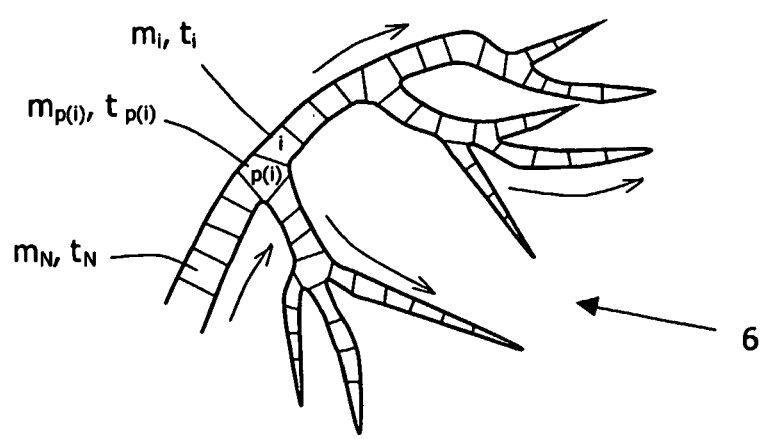
FIG. 2 shows the definition of variables and indices in respect of the three-dimensional model of a vessel tree.

In accordance with FIG. 2, the vessel tree 6 may be divided into individual sections or clusters of volume pixels (voxels), which are identified by an index i=1, ... N. Per definitionem, the greatest index N is assigned to the starting point of the vessel tree. Further, the function p(i) in each case reflects the index of the vessel section located directly in front of the vessel section with index i, viewed in the direction of flow. This function is necessary, in particular in the case of junction points in the vessel tree, because a consecutive numbering of both vessel branches in steps of units is not possible here.

Once the vessel tree has been established using a first series of angiographic X-ray images, a second image series is produced, in which the X-ray apparatus 1 is preferably stationary, i.e. does not rotate around the patient 2.

During the second image series, a contrast medium is injected—e.g. via a catheter—into the vessel system of the patient 2, and the resultant propagation of the contrast medium in the vessel system is followed on the generated X-ray projections. Using image processing methods, for every section i of the vessel tree, the associated bolus arrival time $m_i$ may be determined from the projection images. This is the time required by the contrast medium from the moment of injection until the vessel section i is reached. The bolus arrival times may serve for describing the flow characteristics in the vessels, and from them may be calculated, for example, the local flow rates. As already mentioned, however, the measured bolus arrival times $m_i$ are subject to a high degree of noise as a result of numerous interference effects. They therefore frequently infringe fundamental physiological boundary conditions, such as the monotony of the progressive flow propagation. This means that a vessel section located further back in the direction of flow may have a shorter measured bolus arrival time mi than a section location in front of it.

To eliminate this problem and to generate a stable reconstruction of the flow characteristics in the vessel system, the calculation of a model propagation is proposed in the form of model bolus arrival times $t_i$ which, in the context of a global optimization, fulfill the monotony condition and are simultaneously as close as possible to the measured data. With the nomenclature introduced above, the monotony condition for the model bolus arrival times $t_i$ sought may be expressed by the following equation:

$$\Delta_i = t_i - t_{p(i)} \geq 0 \quad \forall i=1, \ldots N-1 \tag{1}$$

Observing this boundary condition, the cost function:

$$E = \sum_{i=1}^{N} |m_i - t_i| \tag{2a}$$

which quantifies the discrepancy between the measured and modeled bolus arrival times, as calculated over the entire vessel progression, is now to be minimized. The calculation of the sought variables $t_i$ may hereby take place using linear programming (see D. G. Lünenberger: "Linear and Nonlinear Programming", Addison-Wesley, Reading, 2nd edition, 1984; W. H. Press, S. A. Tuekolsky, W. T. Vetterling, B. P. Flannery: "Numerical Recipes in C", chapter 10.8, University Press, Cambridge, 2nd edition, 1992). With the normal form of this technology, the aim is to minimize the function:

$$F = \overline{c} \cdot \overline{a} \tag{3}$$

while observing the boundary conditions:

$$S \overline{a} = \overline{b} \tag{4}$$

$$a_i \geq 0 \tag{5}$$

wherein $\overline{b}, \overline{c}$ and S are given vectors, or a given matrix, and the vector $\overline{a}$ represents the solution sought.

To be able to use the technology of linear programming for the present problem, two N-dimensional auxiliary vectors $\overline{\epsilon}^+$ and $\overline{\epsilon}^-$ and an N-dimensional auxiliary vector $\overline{\Delta}$ are to be introduced, and the following vectors $\overline{a}, \overline{b}, \overline{c}$ as well as the matrix S are to be defined:

$$\vec{a} = \begin{pmatrix} \vec{t} \\ \vec{\epsilon}^+ \\ \vec{\epsilon}^- \\ \vec{\Delta} \end{pmatrix} \tag{6}$$

$$\vec{b} = \begin{pmatrix} \vec{m} \\ \vec{0}_{N-1} \end{pmatrix} \tag{7}$$

$$\vec{c} = \begin{pmatrix} \vec{0}_N \\ \vec{1}_N \\ \vec{1}_N \\ \vec{0}_{N-1} \end{pmatrix} \tag{8}$$

$$S = \begin{pmatrix} 1_{N \times N} & 1_{N \times N} & -1_{N \times N} & 0_{N \times (N-1)} \\ P & 0_{(N-1) \times N} & 0_{(N-1) \times N} & -1_{(N-1) \times (N-1)} \end{pmatrix} \tag{9}$$

Here, $\vec{1}_M$ and $\vec{0}_M$ designate M-dimensional vectors, which contain a one or a zero in each component; $1_{M \times M}$ is a unit matrix of the variable M×M; $0_{M \times L}$ is a matrix with M rows and L columns, whose components are all zero; and P is the (N−1)×N coupling matrix, which is defined by:

$$P_{ij} = \begin{cases} 1 & \text{if } i = j \\ -1 & \text{if } p(i) = j \\ 0 & \text{otherwise} \end{cases} \tag{10}$$

Since p(i)≠i, the definition of P is uncontested.

Using the variables defined above, the function:

$$F = \vec{c} \cdot \vec{a} = \sum_{i=1}^{N} (\varepsilon_i^+ + \varepsilon_i^-) \quad (11)$$

is to be minimized by linear programming, observing the boundary conditions:

$$t_i - \epsilon_i^+ - \epsilon_i^- = m_i \text{ for } i=1, \ldots N \quad (12)$$

$$t_i - t_{p(i)} - \Delta_i = 0 \text{ for } i=1, \ldots N-1 \quad (13)$$

$$t_i \geq 0 \quad (14)$$

$$\epsilon_i^+ \geq 0 \quad (15)$$

$$\epsilon_i^- \geq 0 \quad (16)$$

$$\Delta_i \geq 0 \quad (17)$$

Equation (11), together with equations (12), (14)-(17), implies that, for each index i=1, ... N, either $\epsilon_i^+$ or $\epsilon_i^-$ has to be zero. If, for example, $\epsilon_i^- \geq \epsilon_i^+ > 0$, with the formula $\tilde{\epsilon}_i^- := \epsilon_i^- - \epsilon_i^{30}$, $\tilde{\epsilon}_i^+ = 0$ a smaller value would be obtained in equation (11). Since in addition $$\epsilon_i = \epsilon_i^+ - \epsilon_i^- = m_i - t_i \quad (18)$$

the minimization of the variable F in equation (11) is equivalent to the minimization of E in equation (2a). In a similar manner, the secondary condition defined in equation (1) is equivalent to equations (13) and (17). The solution for equations (11)-(17) that can be determined with standard methods of numerical mathematics thereby simultaneously supplies the solution to the minimization problem of equations (1) and (2a), provided the measurement data is sufficiently great to ensure the secondary condition $t_i \geq 0$. The latter can, however, be achieved in a simple manner by the addition of a constant to all measurement data.

It is pointed out that there is a so-called permitted base vector, i.e. a vector $\bar{a}$, which fulfils all boundary conditions. With the definition:

$$\iota = \max\{m_i | i=1, \ldots N\} \quad (19)$$

the vector $\bar{a}$ may be composed of the following components:

$$\bar{t} = (\iota, \ldots \iota)^T \quad (20)$$

$$\bar{\epsilon}^+ = (0, \ldots 0)^T \quad (22)$$

$$\bar{\epsilon}^- = (\iota - m_1, \ldots \iota - m_N)^T \quad (22)$$

$$\bar{\Delta} = (0, \ldots 0)^\iota. \quad (23)$$

The method explained above may, in addition, be supplemented, in the context of a regularization, by a criterion that demands a smooth progression of the solution. In this regard, in addition to equation (2a), the sum of the absolute values of the second derivatives of the bolus arrival times $t_i$ is to be minimized below.

To this end, a further set of variables $\delta_1^+, \ldots \delta_{N-M-1}^+$ and $\delta_1^-, \ldots \delta_{N-M-1}^-$ is defined. Here, M stands for the number of vessel sections without successors, i.e. the downstream ends of the vessel tree under consideration. Notwithstanding the general principles, an indexing in which these M vessel sections have the very indices N-M, ... N-1 may hereby be required. For each index i=1, ... (N-M-1), $\delta_i^+ - \delta_i^-$ is to represent the second derivative of the bolus arrival times in the case of vessel section i. These variables therefore have to be linked to the vector of the bolus arrival times $\bar{t}$ by the following boundary condition:

$$\delta_i^+ - \delta_i^- = t_{p(i)} - 2t_i + \frac{1}{|J|}\sum_{j \in J} t_j \text{ with } J = \{j \mid p(j) = i\} \quad (24)$$

Here, |J| corresponds to the number of vessel sections that have the vessel section i as their predecessor. Apart from junction points in the vessel tree, the vessel section i has only one successor j, so |J|=1 and the right-hand side of equation (24) collapses for the usual discrete approximation of the second derivative. If the length of the individual vessel sections within the vessel tree varies greatly, the introduction of geometric weightings may be advisable.

Linear programming may now be used to minimize the following variable:

$$E_m = \sum_{i=1}^{N-M-1} (\delta_i^+ + \delta_i^-) = \sum_{i=1}^{N-M-1} |t_i''| \quad (2b)$$

A small value of $E_m$ hereby means that the absolute values of the second derivatives of the bolus arrival times are small. Therefore, "smooth" solutions $\bar{\tau}$ are preferred.

The regularization further requires the introduction of a regularizing parameter $\lambda$, which weights the two target functions to be minimized, i.e. the "data term" E in accordance with equation (2a) and the "model term" $E_m$ in accordance with equation (2b).

The variables used for linear programming may then be assumed in accordance with equations (26) to (29) of FIG. 3, wherein l=N-M-1 is written for simplification purposes. The additional I×N coupling matrix C implements the right-hand side of the condition of equation (24) and is defined in accordance with equation (30) of FIG. 3.

During regularization, it is generally difficult to select a "good" value for the regularization parameter $\lambda$ in advance. To overcome this problem, a two-stage method is proposed here. In the first stage, the optimization is executed without regularization. This provides a first estimation $\bar{t}^{(0)}$ for the bolus arrival times, with which the "best possible" data term $E^{(0)}$ is then calculated, i.e.

$$E^{(0)} = \sum_{i=1}^{N} |m_i - t_i^{(0)}|. \quad (31)$$

A value for E that is achievable more practically may now be assumed, e.g. $E = sE^{(0)}$ with s>1. Since everything is linear, the original minimization of E may be replaced by the condition $E = sE^{(0)}$, which leads to equations (32) to (35) in FIG. 3 for the linear programming.

In accordance with equation (36), it is further possible to find a permitted base vector. It may be necessary, in turn, to shift all values $t_i^{(1)}$ if the obtained $t_N^{(1)}$ is negative.

Alternatively, the worst case model term $E_m^{(0)}$ may also be calculated, based on the first vector $\bar{t}^{(0)}$ and the condition $E_m = sE_m^{(0)}$ with s<1 may be added to the minimization problem of the data term E.

Finally, it should be pointed out that the method described also permits the integration of other physiological information, which may be described in the form of linear boundary conditions. For example, the mass preservation could be formulated in this manner.

The invention claimed is:

1. A data processing device for reconstructing the current flow in a vessel system, comprising a memory with measurement data ($m_i$) describing an observed progressive propagation of a medium in the vessel system, wherein the data processing device is configured to reconstruct, from the measurement data, a model propagation ($t_i$) of a medium within the vessel system in such a way that, for the vessel system:
   a difference between an observed propagation and a model propagation is minimal, and
   a model propagation is monotonously progressive.

2. A data processing device as claimed in claim 1, configured to reconstruct the model propagation ($t_i$) in such a way that it additionally has as smooth as possible a progression.

3. A data processing device as claimed in claim 1, wherein the memory contains, as measurement data, bolus arrival times $m_i$, wherein i=1, . . . N are indices for various individual sections of the vessel system, and a bolus arrival time $m_i$ is a time, determined in a measurement, which a medium requires, starting from a predetermined starting point, to reach vessel section i.

4. A data processing device as claimed in claim 3, wherein the device is configured to calculate model bolus arrival times ($t_i$) for the vessel sections i in such a way that:

$$\Delta_i = t_i - t_{p(i)} \geq 0 \; \forall \; i=1, \ldots N-1 \quad (1)$$

and the cost function $$E = \sum_{i=1}^{N} |m_i - t_i| \quad (2a)$$

is minimal, wherein the values p(i) each hereby reflect the index of the vessel section located in front of vessel section i in a direction of flow.

5. A data processing device as claimed in claim 4, wherein it is configured additionally to take into account in the cost function the variable:

$$E_m = \sum_{i \in I} |t_i''| \quad (2b)$$

wherein I contains the indices of all vessel sections with a predecessor and a successor, and $t_i''$ is the discrete approximation of the second derivative in vessel section i.

6. A data processing device as claimed in claim 4, wherein it is configured to calculate the model bolus arrival time ($t_i$) using linear programming.

7. A data processing device as claimed in claim 1, wherein it is coupled with a display device (7) in order that the model propagation may be graphically represented.

8. An assembly for observation of the current flow in a vessel system, comprising an image-generating device for generating images of the vessel system, from which measurement data ($m_i$) describing the progressive propagation of a medium may be obtained, and a data processing device as claimed in any one of claims 1 to 7 for reconstructing the current flow in the vessel system.

9. An assembly as claimed in claim 8, wherein the image-generating device is an X-ray apparatus (1).

10. A method of reconstruction the current flow in a vessel system, comprising the following steps:
   a) Obtaining measurement data ($m_i$) describing an observed progressive propagation of a medium in the vessel system;
   b) Reconstructing a model propagation ($t_i$) of a medium in the vessel system in such a way that:
   a difference between an observed propagation and a model propagation is minimal, and
   a model propagation is monotonously progressive.

* * * * *